(12) United States Patent
Brambilla et al.

(10) Patent No.: US 6,841,378 B1
(45) Date of Patent: Jan. 11, 2005

(54) **PRODUCTION OF HETEROLOGOUUS PROTEINS FROM *ZYGOSACCHAROMYCES BAILII***

(75) Inventors: Luca Brambilla, Milan (IT); Bianca Maria Ranzi, Milan (IT); Marina Vai, Milan (IT); Lilia Alberghina, Milan (IT); Danilo Porro, Milan (IT)

(73) Assignee: Biopolo S.C.R.L., Milan (IT)

( * ) Notice: Subject to any disclaimer, the term of this patent is extended or adjusted under 35 U.S.C. 154(b) by 0 days.

(21) Appl. No.: 10/130,061

(22) PCT Filed: Jan. 14, 2000

(86) PCT No.: PCT/EP00/00268

§ 371 (c)(1),
(2), (4) Date: May 15, 2002

(87) PCT Pub. No.: WO00/41477

PCT Pub. Date: Jul. 20, 2000

(30) Foreign Application Priority Data

Jan. 15, 1999 (IT) .......................................... MI99A0065

(51) Int. Cl.[7] ........................... C12P 39/00; C12P 21/06; C12N 15/00; C12N 1/12; C07H 21/04
(52) U.S. Cl. ................................. 435/254.21; 435/69.1; 435/320.1; 435/41; 435/252.1; 435/243; 435/25; 435/471; 536/24.1; 536/23.1
(58) Field of Search ...................... 435/41, 69.1, 252.1, 435/254.21, 243, 320.1, 25, 471, 193, 183, 202, 325, 172.3; 536/24.1, 23.1, 23.2

(56) References Cited

U.S. PATENT DOCUMENTS 4,626,505 A * 12/1986 Falco .............................. 435/6
2002/0034805 A1 * 3/2002 Gilbert et al. .............. 435/193

OTHER PUBLICATIONS

Thompson et al. An Improved Protocol for the Preparation of Yeast Cells for Transformation by Electroporation. Yeast vol. 14:pp 565–571, 1998.*
A.J.C. Steyn et al., "Co-expression of a *Saccharomyces diastaticus* glucoamylase-encoding gene and a *Bacillus amylolique-faciens* α-amylase-encoding gene in *Saccharomyces cerevisiae*", Gene, vol. 100, 1991, pp. 85–93.
Ogawa Yoshihiro et al., "Secretion of *Aspergillus oryzae* Alkaline Protease in an Osmophilic Yeast, *Zygosaccharomyces rouxii*", Agricultural and Biological Chemistry, vol. 54, No. 10, 1990, pp. 2521–2529.
Kohei Ushio et al., "Construction of a Host-Vector System in the Osmophilic Haploid yeast *Zygosaccharomyces rouxii*", Journal of Fermentation Technology, vol. 66, No. 5, 1988, pp. 481–488.
Kuyo Utatsu et al., "Yeast Plasmids Resembling 2 μm DNA: Regional Similarities and Diversities at the Molecular Level", Journal of Bacteriology, vol. 169, No. 12, 1987, pp. 5537–5545.
Kohji Sugihara et al., "Ribosomal DNA Plasmid Isolated from *Zygosaccharomyces bailii* and Its Use for Constructing Yeast Vectors Effective for Intergeneric Gene Transfer", Agricultural and Biological Chemistry, vol. 50, No. 6, 1986, pp. 1503–1512.
E. Martinez et al., "Rapid Transformation of Non-Saccharomyces Yeasts by Electroporation", Biotechnology Techniques, vol. 7, No. 12, 1993, pp. 895–896.

* cited by examiner

*Primary Examiner*—Gerry Leffers
*Assistant Examiner*—Maria Marvich
(74) *Attorney, Agent, or Firm*—Williams, Morgan & Amerson, P.C.

(57) ABSTRACT

The production of recombinant gene products from cultures of the yeast *Zygosaccharomyces bailii* strains transformed with expression vectors bearing the gene coding for the proteins.

2 Claims, 4 Drawing Sheets

FIGURE 1-A
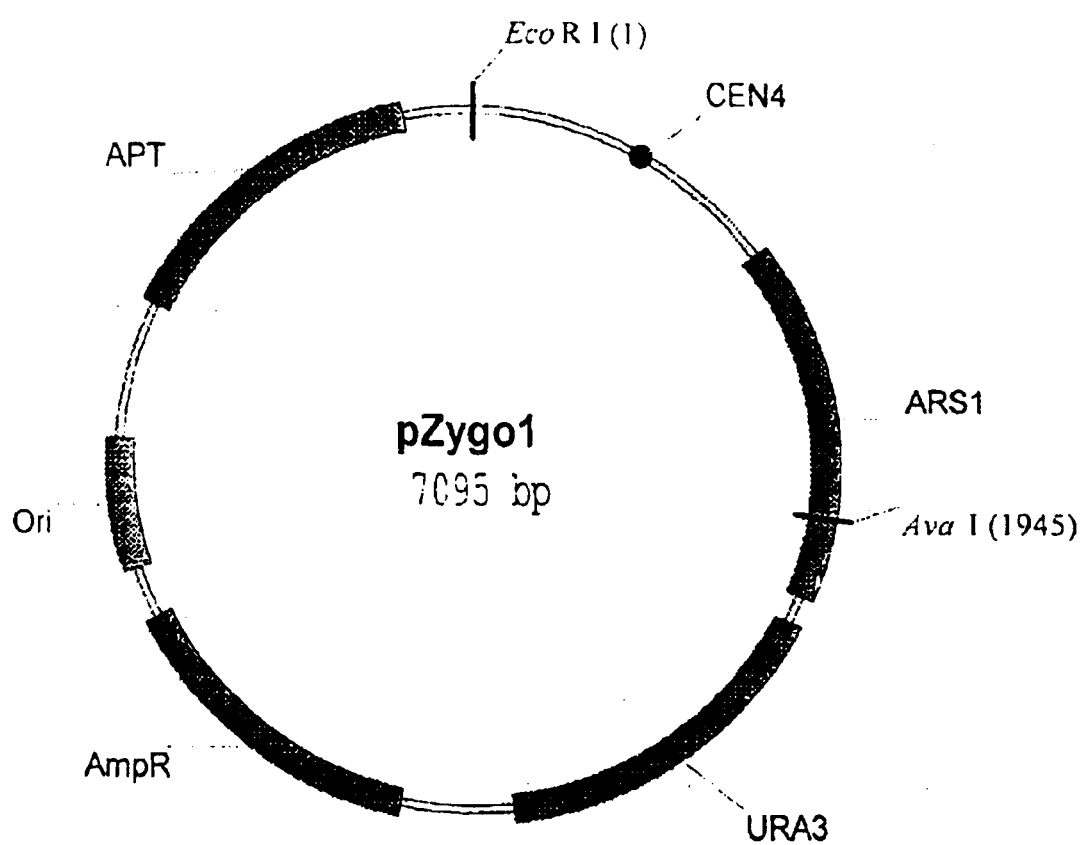

FIGURE 1-B
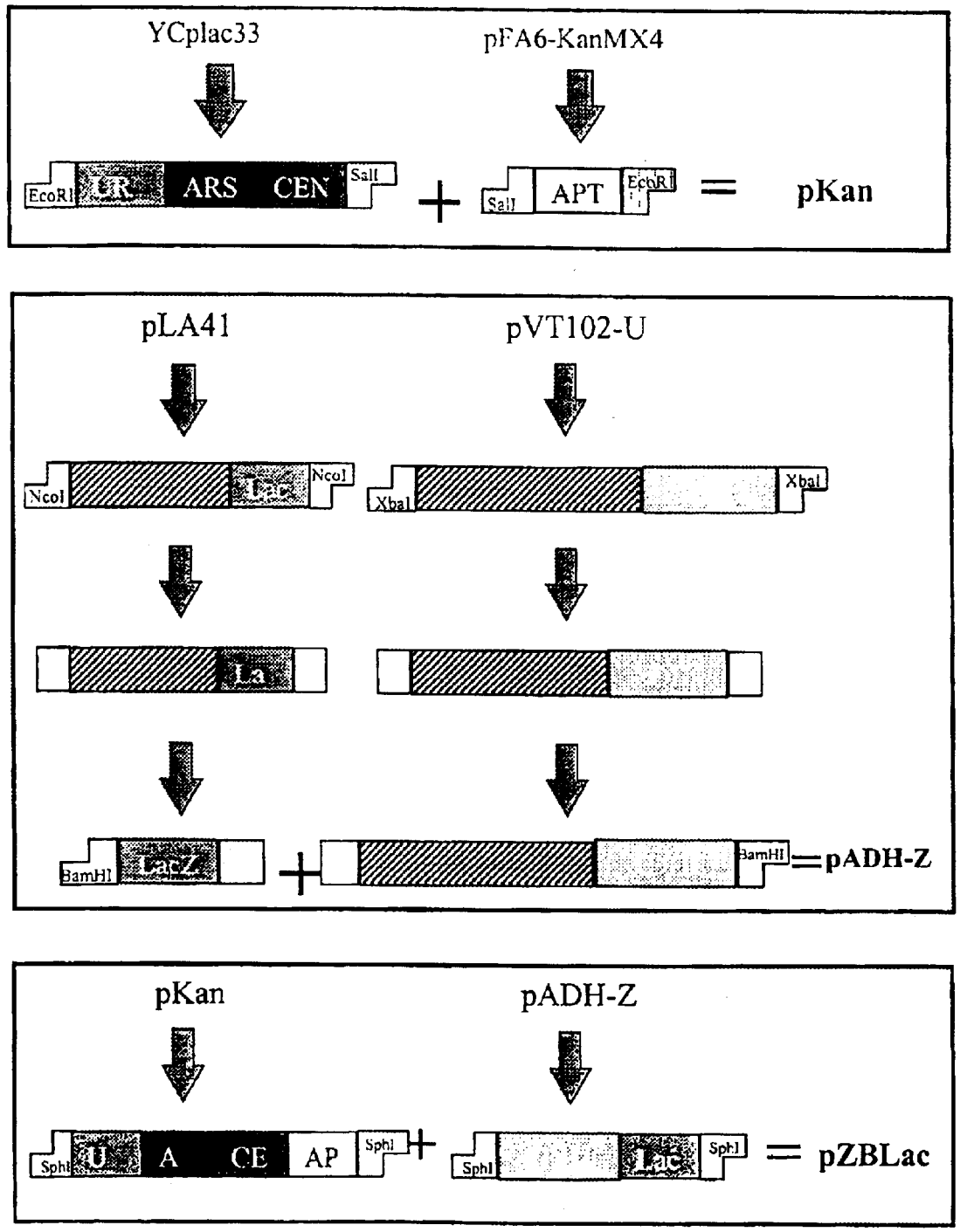

FIGURE 1-C
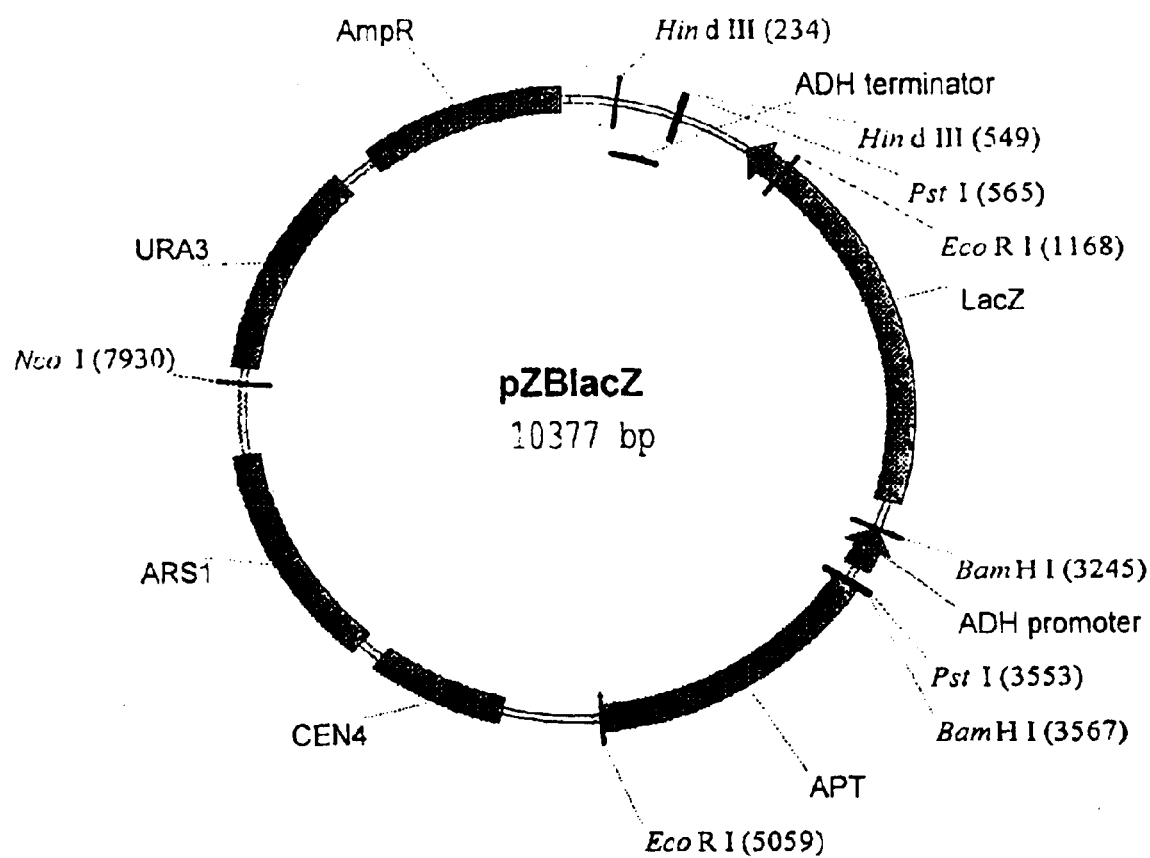

US 6,841,378 B1

PRODUCTION OF HETEROLOGOUUS PROTEINS FROM *ZYGOSACCHAROMYCES BAILII*

FIELD OF THE INVENTION

The invention refers to the production of recombinant gene products from cultures of strains of the yeast *Zygosaccharomyces bailii* transformed with expression vectors bearing the gene coding for said proteins.

BACKGROUND OF THE INVENTION

Recombinant DNA technologies (also known as genetic, protein and metabolic engineering) allow the production of a wide range of peptides and proteins in cells which do not naturally produce such peptides and proteins. The introduction of a heterologous as well as of a homologous gene, along with controlling sequences, in the selected host could lead to large accumulation of useful products: for example, proteins, enzymes, hormones or antigens. The availability of significant amounts of proteins is often a highly desirable goal. For example, in the pharmaceutical field, pre-clinical and clinical trials often require substantial amounts of potentially interesting recombinant proteins. Some recombinant products are already available on the market (such as growth hormone, Tissue Plasminogen Activator, hepatitis B virus vaccine, interferons, and erythropoietin), and many more are currently in the last phase of clinical trials. Production of recombinant proteins also has applications in other industrial sectors. Some recombinant products are used in the food industry (e.g., β-galactosidase, chymosin, amylases, glucoamylase, and amyloglucosidase) as well as in the textile and paper industries (e.g., proteases, amylases, cellulases, lipases, and catalases). Recombinant enzymes are useful as detergents (proteases, lipases and surfactants), and their characteristics of stereo-specificity are exploited in a wide number of bioconversions, often yielding desired chiral compounds. A promising field is the application of recombinant enzymes for the development of biosensors. The potential applications of the biosensor technology range from human health to environmental monitoring and the control of industrial bioprocesses. Finally, a very interesting class of heterologous expressed genes are those which give new metabolic abilities to the host cells, allowing the use of non-conventional substrates (e.g., whey, phenols, starch, lignin, and cellulose). On the other hand, metabolic engineering could increase the production of fine chemical metabolites, such as organic acids (e.g., lactic acid), amino acids (e.g., glutamic acid), vitamins, and solvents (e.g., ethanol, 1-2 propanediol, and butanol).

The first requisite for a successful process based on engineered cells for the production of recombinant gene products concerns the choice of the host and of the expression vector. The choice must consider different factors such as product complexity, host characteristics and production level of the desired protein. From a chronological point of view, the first hosts used for the production of heterologous proteins were prokaryotes: *Escherichia coli* and *Bacillus subtilis*; later on, eukaryotic host cells were also used, particularly *Saccharomyces cerevisiae* (*S. cerevisiae*).

The yeast *S. cerevisiae*, commonly considered a safe organism, has been used for centuries in food processes. Moreover, it is a well-known microorganism: its genome has been completely sequenced and its physiology and biochemistry have been studied for a long time. This yeast is able to perform some post-translational modifications of heterologous protein products, which often are important for retaining biological activity; such posttranslational modifications cannot usually be obtained using a prokaryotic host. Finally, it is possible to drive the secretion of the desired product directly into the growth medium, thus improving the large-scale recovery and purification of a correctly folded, homogeneous product. Along the years, *S. cerevisiae* has been developed as a host for the production of both heterologous and homologous gene products with applications in many important fields of modern society (e.g., health care, pharmaceuticals, environment, agriculture, food, and chemistry) (reviewed by: Romanos, M. A., Scorer, C. A. and Clare, J. J. (1992) Yeast 8:423–488; Sudbery, P. (1996) Curr. Op. Biotechnol. 7:517–524; and Lin Cereghino, G. P. and Cregg, J. P. (1999) Curr. Op. Biotechnol. 10:422–427).

Independently of the source of the host cells, exploiting rDNA techniques for the production of recombinant gene products requires a number of considerations. The coding sequence of the gene of interest must be compatible with the chosen host. The starting codon must be unequivocally recognized; codons coding for the amino acids of the heterologous protein must be complemented by anticodons of the host's tRNA and, preferably, should correspond to the most representative tRNAs in the tRNA pool of the said host. Moreover, if present, signals for post-translational modifications must be the same as, or compatible with, those of the host cell. The recombinant gene, having the above characteristics, must be placed under the control of sequence (s) regulating transcription and translation in the host cell. The recombinant gene and the regulating sequence(s) can be referred to as an expression cassette. The promoter and the terminator regulating sequences must be carefully chosen, since they directly affect the expression levels. Other sequences can determine the fate of the recombinant protein, sorting it in the vacuole, into the nucleus, into the mitochondria, or along the secretion pathways. Also, the stability of the mRNA and its affinity for the translation machinery are affected by the nucleotide sequence. Once the expression cassette has been constructed, it has to be inserted into an expression vector and introduced into the recipient host cell. To this aim, several solutions are available.

The expression cassette can directly be inserted in the genome of the host, by means of recombination, which can be either homologous (between two identical sequences, and thus requiring knowledge of the target sequence) or heterologous (at a position in the genome which cannot be controlled). A selective marker is usually required. Auxotrophic markers complement a nutrient request, allowing the growth of the recombinant cells on non-supplemented medium. Dominant markers are genes conferring the resistance to some toxic compounds, so that only cells bearing such a marker can grow on selective media.

Alternatively, it is possible to use episomal vectors, commonly referred to as plasmids. Such vectors are DNA fragments able to replicate themselves in host cells. There are different kinds of episomal vectors, depending on the host. For the well known host *S. cerevisiae*, exemplary episomal vectors include those reported by Rose, A. B. and Broach, J. R. (1990) Methods Enzymol 85:234–279; Schneider, J. C. and Guarente, L. (1991) Methods Enzymol 194:373–388; Romanos, M. A. et al., supra; and Fukuhara, H. (1995) FEMS Microbiol. Letters 131:1–9. Specific examples include:

In the 2μ-like plasmid, the heterologous gene is inserted in a vector bearing all or part of the sequences from the native 2μ plasmid of *S. cerevisiae*. The plasmid is extremely stable without selective pressures.

The ARS plasmid is a quite unstable vector based on an ARS endogenous sequence, which promotes DNA replication at the time of chromosomal replication.

The Centromeric plasmid is essentially an ARS vector that is stabilized by the addition of a centromeric sequence (CEN); these CEN sequences drive a correct partition of the vectors during mitosis. It is a very stable vector, but is retained at a low copy number (1–2/cell).

Linear plasmids, which comprise double-stranded DNA or RNA sequences, are quite common in yeasts, and theoretically could be used in strains lacking 2µ-like plasmids. To date, no significant data are available for such a use.

A Minichromosome, based on a very long DNA fragments, is very stable as a result of the presence of telomers, in addition to the above-described ARS and CEN sequences. Minichromosomes are often used for basic research purposes. Potentially they can be used to clone a large cluster of genes, such as a complete heterologous metabolic pathway.

From the comparison of the expression levels of a large set of recombinant proteins obtained in several host cells, it is apparent that the ideal host cell is not yet available. In fact, each species has some drawbacks that should be carefully evaluated, as each species' drawbacks can be only partially overcome by a good strategy of production. These drawbacks justify research into new host cells, in which negative traits are absent or attenuated.

Bacterial hosts have been used for the production of heterologous proteins, typically the well-known *E. coli*. Since heterologous products for food and pharmaceutical applications must be free from any toxic or dangerous compounds, bacterial cells do not represent the ideal host for applications in the above-cited industrial sectors. *E. coli* produces some toxic or potentially toxic metabolites, which must be removed with careful purification protocols. Moreover, yields of heterologous products are often lowered by the formation of large insoluble aggregates, commonly called inclusion bodies. Further, *E. coli* typically possesses strong proteolytic activity, which can be detrimental to the production of heterologous proteins. *S. cerevisiae* offers many advantages for the production of recombinant gene products; unfortunately, this host is unable to utilize some very cheap carbon sources, such as starch and whey. Furthermore, this host produces high amounts of ethanol when grown in the presence of relatively high sugar concentrations; the ethanol production (determined by the Crabtree effect) can be overcome with a careful (but not economically feasible) monitoring of the fermentative conditions. The high ethanol production lowers biomass yields and, consequently, yields of the heterologous gene product. Moreover, this yeast has a secretion apparatus not suitable for the very high production levels required for industrial purposes. Finally, the secreted proteins are often hyperglycosylated when compared to the natural product, and therefore it is hard to obtain the production of a protein identical to the original one.

Recently, expression of recombinant gene products has been obtained in some non-conventional yeasts: *Hansenula polymorpha, Pichin pastoris, Kluyveromyces lactis* and *Yarrowia lipolytica* (reported in Buckholz, R. G. and Gleeson, M. A. G. (1991) Bio/Technology 9:1067–1072; Fleer, R. (1992) Curr. Op. Biotechnol. 3:486–496; Gellissen, G. and Hollenberg, C. P. (1997) Gene 190: 87–97; Muller, S., Sandal, T., Kamp-Hansen, P. and Dalboge, H. (1998) Yeast 14: 12671283; and Lin Cereghino, G. P. and Cregg, J. P., supra). Said yeasts display some interesting attributes when compared to *S. cerevisiae*, such as possibly better expression levels, or favorable growth characteristics such as high efficiency of growth on low-cost substrates or ability to grow under severe culture conditions. (Sudbery, P. E., (1994) Yeast 10: 1707–1726, Romanos, M. A. et al., supra; Lin Cereghino, G. P. and Cregg J. P., supra).

Another non-conventional yeast seems to offer many advantages when compared to *S. cerevisiae* host cells: *Zygosaccharomyces bailii*. This yeast displays an exceptional resistance to several stresses. For this reason, it is one of the main economically relevant spoilage yeasts. In fact, this yeast can grow in media with low water availability, high hydrostatic pressure (Palou E., Lopez-Malo A., Barbosa-Canovas G. V., Welti-Chanes J., Davidson P. M., Swanson B. G. (1998) J. Food Proto 61:1657–60) and (relative to *S. cerevisiae*) high temperatures (Makdesi A. K. and Beuchatlo R. (1996) Int. J. Food Microbiol. 33: 169–81). In addition, it tolerates high sugar concentrations. Another remarkable characteristic is its very good tolerance to acidic environments, as it grows at pH values as low as 2, and with high partial $CO_2$ pressures. Further, this yeast can survive to high preservative concentrations, such as 600 mg/l of benzoic acid (Makdesi et al., supra) or to sorbic acid (Cole M. B., Keenan M. H. (1986) Yeast 2:93–100). However, physiology studies and molecular genetic tools for the genus Zygosaccharomyces are very poor: as of Dec. 28, 1999 only 11 genetic sequences from *Z. bailii* and 38 from *Z. rouxii* were available at the Internet site GenBank, and only a fraction of the genetic sequences code for proteins. Six different endogenous plasmids have been isolated from the genus Zygosaccharomyces: pSR1, from *Z. rouxii*, pSB2 from *Z. bailii*, pSM1 from *Z. fermentati*, and pSB 1, pSB3 and pSB4 from *Z. bisporus*. They are structurally and functionally related, but they do not share sequence homology among themselves or with the 2µ endogenous plasmid of *S. cerevisiae*, so that they usually are not maintained in different species. Plasmid pSR1 (6251 bp), the endogenous plasmid of *Z. rouxii*, is the most studied in this genus. Its structure resembles that of the 2µ plasmid of *S. cerevisiae*, and displays a pair of inverted repeat sequences between 2 unique sequences, bearing 3 genes (R, recombinase; P and S, stability) and the sequence Z, a cis-acting locus involved in maintenance of the plasmid. Each of the repeated sequences contains an ARS, which is also recognized by *S. cerevisiae* (Araki, H., Jearnpipatkul, A., Tatsumi, H., Sakurai, T., Ushio, K., Muta, T. and Oshima, Y. (1985) J. Mol. Biol. 182:191–203). Since the sequences recognized by the recombinase are not completely overlapping (Araki, H. and Oshima, Y. (1989) J. Mol. Biol. 207:757–69), the 2µ plasmid cannot replicate in *Z. rouxii*. Proteins P, R and S are also characterized in that they cannot complement between *Z. rouxii* and *S. cerevisiae* (Araki et al. (1985) supra).

Unlike the plasmid replication origin from *S. cerevisiae*, the ARS 1 chromosomal replication origin from *S. cerevisiae* is recognized by *Z. rouxii*: a centromeric plasmid with this sequence could be stably maintained (Araki, H., Awane, K., Irie, K., Kaisho, Y., Naito, A., and Oshima, Y. (1983) Mol. Gen. Genet. 238: 120–8).

The molecular mechanisms for plasmid replication and repartition are not transferable among the Zygosaccharomyces yeast strains: this is the case of pSR1 and pSB3 (Utatsu, I., Utsunomiya, A., and Toh-e, A. (1986) J. Gen. Microbiol. 132:1359–65). This fact is not surprising, as sequences of all the isolated plasmids are very different, except for a certain homology between pSB1 and pSB4. Usually, *S. cerevisiae* is the less restrictive yeast, as it can recognize ARS sequences from other sources; on the other hand, no one of the Zygosaccharomyces strains tested so far was able to replicate a plasmid bearing ARS sequences from the *S. cerevisiae* 2µ natural plasmid.

Few attempts were made to apply knowledge of the genetics of the yeast *Z. rouxii* for the production of heterologous proteins. The only example concerns the expression of alkaline protease from *Aspergillus oryzae*. The expression system is based upon the endogenous pSR1 plasmid, and the use of the endogenous promoter GAPDH; geneticin (G418) resistance is the dominant marker (Ogawa, Y., Tatsumi, H., Murakami, S., Ishida, Y., Murakami, K., Masaki, A., Kawabe, H., Arimura, H., Nakano, E., Motai, H. et al., (1990) Agric. & Biol. Chem. 54:2521–9).

Knowledge of the genetics of *Z. bailii* is even lower. The endogenous plasmid pSB2 (5415 bp) shows some analogies with pSR1 (Toh-e, A., Araki, H., Utatsu, I., and Oshima, Y. (1984) J. Gen. Microbiol. 130: 2527–34; Utatsu, I., Sakamoto, S., Imura, T., and Toh-e, A. (1987) J. Bacteriol. 169:5537–45). In addition, some linear double stranded RNA plasmids have been described. (Radler, F., Herzberger, S., Schonig, I., and Schwarz, P. (1993) J. Gen. Microbiol. 139:495–500). Very recently, some information appeared about the development of genetic tools for *Z. bailii*. A genomic bank of the yeast has been obtained (Rodrigues, F., Zeeman, A. M., Sousa, M. I., Steensma, H. Y., Corte-Real, M., and Leao, C. (1999) In: Proceedings of the XIX International Conference on Yeast Genetic and Molecular Biology, Curr. Genet. 35:462) and the disruption of the URA3 gene has been also described (Mollapour, M. and Piper, P. W. (1999) In: Proceedings of the XIX International Conference on Yeast Genetic and Molecular Biology, Curro Genet. 35:452). However, nothing has to date been published about homologous or heterologous protein expression obtained from this yeast.

Since *Z. bailii* yeasts can grow in very restrictive cultural conditions (e.g., pH, ionic strength, temperature, sugar concentration, and acid concentration), they are potentially interesting from an industrial point of view. In fact, the features described above greatly simplify many fermentation procedures. For example, there is no need for strict and sophisticated control of process parameters and of medium composition. Moreover, the ability to grow at higher temperature facilitates heat control, one of the primary problems arising during high density, large-scale fermentations. Finally, fermentation in restrictive conditions prevents contamination problems, thus reducing the need for expensive sterilization steps. All those elements, together with a high specific productivity, are essential to allow the economic success of an industrial production of heterologous protein.

In view of the above considerations, the importance of the development of genetic expression system(s) for *Zygosaccharomyces bailii* strains and a fast and reliable transformation protocol for the production of recombinant proteins (i.e., heterologous and/or homologous) in such a host are clear.

SUMMARY OF THE INVENTION

According to a first embodiment, this invention provides *Zygosaccharomyces bailii* strains transformed with at least one copy of a recombinant DNA gene functionally linked to promoter sequences allowing the expression of said gene in this yeast.

The invention also provides an expression vector which allows the introduction and replication of a recombinant (rDNA) gene, either homologous or heterologous, functionally linked to a promoter sequence for the production of the recombinant product.

According to a further embodiment, the invention provides a process for the production of heterologous proteins by culturing the above described engineered yeast strains in a fermentation medium and recovering the recombinant gene product from said fermentation medium.

DESCRIPTION OF THE INVENTION

It has been found that the expression of heterologous proteins can be obtained by modified *Zygosaccharomyces bailii* yeasts.

More particularly, it has been found that expression vectors useful for the introduction of genetic material into the yeast *Z. bailii* and for the subsequent production and recovery of recombinant gene products can be developed starting from the ARS sequences of the yeast *S. cerevisiae*. It has been found that such sequences, and in particular the sequence ARS1 (Tschumper, G. and Carbon, J. (1980), Gene 10: 157–166), once introduced in the host cell *Z. bailii*, allow the autoreplication of the expression vector. Any ARS-like sequence, isolated from the yeast genus Zygosaccharomyces, and especially from *Z. bailii*, or from similar yeasts, can be used. The development of expression vectors containing all or part of the endogenous pSB2 plasmid, along with the expression cassette and a transformation marker, is also possible.

It has been found that the APT gene (Hadfield, C., Jordan, B. E., Mount, R. C., Pretorius, G. H. J., and Burak, E. (1990) Curr. Genet. 18:303–313), coding for resistance to the antibiotic geneticin (G418), can be used as a transformation marker for the selection, propagation, and growth of recombinant clones. Other dominant markers are available for yeasts (e.g., formaldehyde resistance, phleomycin resistance, and fluoroacetate resistance, among others, reviewed in Van den Berg, M. and Steensma, Y. H. (1997), Yeast 13:551–559), and have a good chance of being active in *Z. bailii* as well. A description of the use of SFA1 gene, encoding formaldehyde resistance, in *Z. bailii* has been very recently reported (Mollapour, M. and Piper, P. W., supra).

Alternatively, auxotrophic markers from other yeasts as well as from *Z. bailii* can be successfully also used. In fact, the rescue of auxotrophic deficiency of *S. cerevisiae* (ura3, his3, trp1 and leu2) with sequences isolated from *Z. bailii*, probably coding for homologous gene products, has been shown. It is therefore likely that those auxotrophic markers can be "shuttled" between said yeasts (Rodrigues et al., supra; Mollapour, M. and Piper, P. W., supra).

It has been found that the stability of the expression vector is strongly increased, even in absence of the selective pressure, by the presence of CEN sequences, and in particular the sequence CEN4 (Mann, C. and Davis, R. W. (1986) Mol Cell Biol, 6:241–245) from *S. cerevisiae*. These sequences drive the correct repartition of the plasmids during cellular division. It follows that other CEN sequences, either homologous or derived from *S. cerevisiae* or other organisms, can also be successfully used.

Vectors may also bear sequences ensuring their propagation in *Escherichia coli* and/or in *S. cerevisiae*.

The transformation protocol we have developed avoids enzymatic digestion of the cell wall, which is a common procedure during the transformation of the Zygosaccharomyces genus. The protocol utilizes an electroporation procedure similar to those already published for *S. cerevisiae* and *Kluyveromyces lactis*. Transformation efficiencies can be increased with a treatment based upon monovalent cations, such as lithium salts, and/or reducing agents, such as dithiothreitol or p-mercaptoethanol, and/or with the addition of nucleic acid as a carrier.

A further increase in the transformation efficiency is obtained by incubation of the treated cells in a regenerative medium. The transformation method is carefully described in Example 3.

The procedure can be applied to all the yeasts of the species *Z. bailii*, preferably to the strains ATTC36947, ATTC60483, and ISA 1307.

According to the present invention, any gene, either prokaryotic or eukaryotic, homologous or heterologous, can be introduced and expressed in *Z. bailii*. The secretion of the recombinant gene product into the culture medium can be obtained by cloning suitable DNA sequences.

This invention can be used for the large scale production of polypeptides having an industrial interest, or giving the transformed strain an industrial interest.

Some examples of proteins that can be produced according to the invention include interferons, growth hormone, Tissue Plasminogen Activator, surface antigen of hepatitis B virus, erythropoietin, interleukins (ILs), colony stimulating factors (CSFs), nerve growth factor (NGF), epidermal growth factor (EGF), insulin-like growth factor (IGF), Tumor Necrosis Factor (TNF), urokinase, clotting factors (XIIIa), β-endorphin, antibodies, agalactosidase, endochitinase, esoglucanase, lysozyme, tetanus toxin, aamylase, glucoamylase, prochymosin, uridine, and xylose isomerase.

The choice of a particular Z. bailii host strain, of the genetic markers, and of the regulating sequences may depend on the particular product. It has been found that expression of heterologous proteins can be preferably obtained using either a constitutive promoter (such as ADH1) or an inducible promoter (such as $GAL_{1-10}$/CYC1) of S. cerevisiae (Porro, D., Martegani, E., Ranzi, B. M., and Alberghina, L. (1991) Appl. Microbiol. Biotechnol. 34:632–636). Other promoters from S. cerevisiae, from other non-conventional yeasts, or from Z. bailii, can also be used for the production of heterologous proteins.

Examples of suitable promoters from S. cerevisiae include: TPI, PGK, GAP, GAL1, ADH1, PHO5, CUP1, Mfα1, and the hybrid promoters GAL/CYC1, GAP/GAL, PGK/GAL, GAP/ADH2, GAP/PHO5, and CYC1/GRE. The preferred promoter is the ADH1 promoter from S. cerevisiae.

The transformation and growth conditions may vary depending on the particular vector used and/or of the particular gene expressed.

BRIEF DESCRIPTION OF THE FIGURES

FIG. 1A. Expression vector: pZYGO1.

FIG. 1B. Schematic representation of the steps necessary for the construction of the pZBlacZ plasmid (for the sake of simplicity, the presence of the terminator sequence of the ADH 1 gene, present downstream of its promoter, is omitted).

FIG. 1C. Diagram of the pZBlacZ plasmid.

Figure 2:
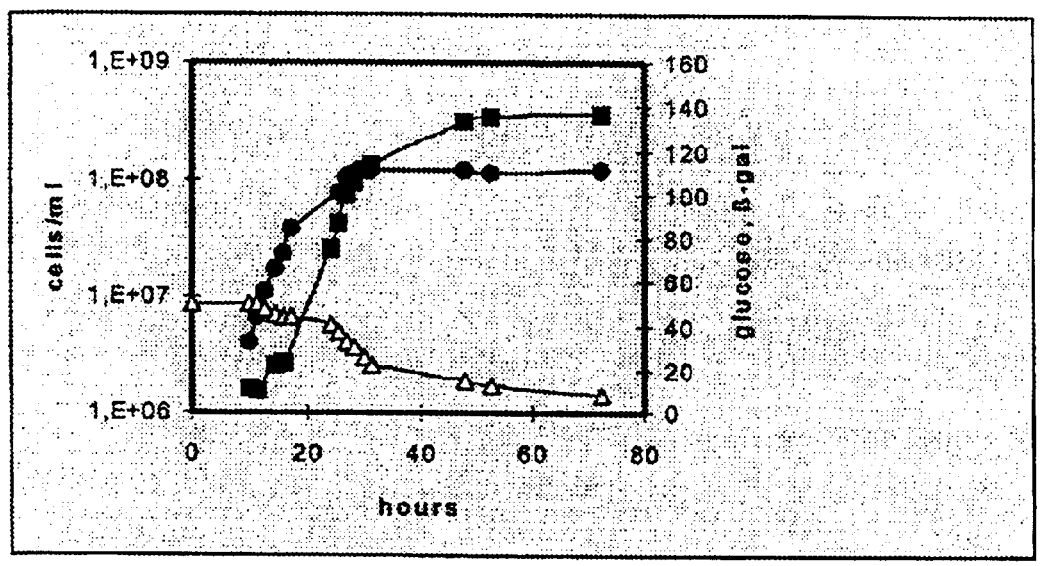
FIG. 2. β-galactosidase production in the Z. bailii ATTC60483 strain during the growth in synthetic medium (YNB with amino acids 13 g/l, glucose 50 g/l, and G418 200 mg/l). Similar results have been obtained using the Z. bailii strains A TTC36947 and ISA1307. Similar results have also been obtained using, instead of the ADH1 promoter, the inducible hybrid promoter $UAS_{GAL1-10}$/CYC1 of S. cerevisiae (data not shown).

(•) Cells/ml; (Δ) glucose, g/l; (■) β-galactosidase, U/mg of total cell proteins.

The invention will be described in more detail by means of the following examples, wherein the expression of a β-galactosidase gene is disclosed.

This experimental model, based on the expression of a well known reporter gene, is of course predictive for the expression of any other gene having industrial interest.

EXAMPLE 1

Construction of pZygo1 Plasmid, a General Expression Vector for Zygosaccharomyces bailii.

Plasmid pZygo 1 is a multi-purpose expression vector, and it contains all the sequences required to self-replicate in three different hosts: Escherichia coli, Saccharomyces cerevisiae, and Zygosaccharomyces bailii. In fact, once provided with the appropriate expression cassette (i.e.: promoter—homologous or heterologous gene—terminator), the same plasmid can be used to assay different level(s) of expression in Zygosaccharomyces bailii, Saccharomyces cerevisiae, and Escherichia coli.

Selection of transformation can be achieved either with the dominant marker APT (in S. cerevisiae or Z. bailii) or with auxotrophic markers, as described above.

The APT gene, enclosed in an EcoRV/SmaI fragment from the plasmid pFA6-KanMX4 (Wach, A., Brachat, A., Pohlmann, R., and Philippsen, P. (1994) Yeast 10: 1793–1808) was subcloned in pBluescript KS+ plasmid (Stratagene) at an EcoRV restriction site. The APT gene confers geneticin (G418) resistance.

Thereafter, the gene was excised with a SalI/EcoRI digestion and inserted at the corresponding sites of the YCplac33 centromeric vector (Gietz, D. R. and Sugino, A. (1988) Gene 74:527–534), thus yielding pZygol. Some unique restriction sites are available along the vector, allowing the insertion of the desired expression cassette (FIG. 1A).

EXAMPLE 2

Construction of the pZBlacZ Plasmid, Containing ADH1 Promoters from S. cerevisiae and a Reporter Gene.

First, vector pKAN was constructed by the insertion of the APT gene, enclosed in a EcoRI/SalI fragment from plasmid pFA6-KanMX4 (Wach, A., Brachat, A., Pohlmann, R., and Philippsen, P. (1994) Yeast 10:1793–1808), at EcoRI and SalI restriction sites of the YCplac33 centromeric vector (Gietz, D. R. and Sugino, A. (1988) Gene 74:527–534).

The LacZ gene from Escherichia coli was obtained in the following way. A first digestion of the plasmid pLA41 by NcoI (Porro, D., Martegani, E., Ranzi, B. M. and Alberghina, L. (1991) Appl. Microbiol. Biotechnol. 34:632636) was followed by a treatment with the Klenow fragment of the enzyme DNA polymerase, in order to obtain blunt end molecules. Those molecules were subsequently digested with BamHI, and a fragment of about 3600 base pairs, containing the coding sequence, was isolated and ligated to the vector pVT102-U (Vemet T., Dignard D. and Thomas D. Y. (1987) Gene 52:225233), previously treated as described hereinbelow. Vector pVT102-U was digested with XbaI, treated with the Klenow fragment and further digested with BamHI. The resulting plasmid, named pADH-Z, bore the LacZ gene under the control of the promoter and the terminator of the ADHI gene from Saccharomyces cerevisiae.

Finally, the whole expression cassette (ADH1 promoter—LacZ gene ADH1 terminator) was excised from pADH-Z by a SphI digestion and inserted into the pKan vector, previously linearized with SphI. The resulting expression plasmid was named pZBlacZ (FIGS. 1B–C).

EXAMPLE 3

Transformation of Zygosaccharomyces bailii Yeasts with pZygol and pZBlacZ.

Z. bailii cells from strains ATTC36947, ATTC60483, and ISA1307 were grown in rich medium YEPD (Yeast Extract 10 g/l, Peptone 20 g/l, Glucose 20 g/l) to a concentration of about $2 \times 10^8$ cells/ml. Cells were collected and incubated for one hour at room temperature, at a density of $1 \times 10^9$ cells/ml, in a freshly prepared solution of 0.1M lithium acetate, 10 mM dithiothreitol, and 10 mM Tris-HCl, pH 7.5. Cells were washed once with water and twice with 1M sorbitol, and concentrated to a density of $1 \times 10^{10}$ cells/ml in 1M sorbitol. Electroporation (1.5 kV, 7.5 KV/cm, 25 μF, 200 Ω: GenePulser, Biorad, Hercules, Calif.) took place in the presence of 3–5 μg of plasmid.

Cells were recovered with an incubation of 18 hours in 5 ml of YEPD and 1M sorbitol at 28°. The selection of transformants was performed by plating the cellular suspension in 20 g/l glucose, 20 g/l Peptone, 10 g/l Yeast Extract, 20 g/l agar, 200 mg/l G418 (Gibco BRL, cat. 11811-031)). Single clones appeared in 2–3 days at 28°.

EXAMPLE 4

Heterologous Protein Production During a Batch Fermentation of *Zygosaccharomyces bailii* (pZBlacZ) Transformed Cells.

Some single clones obtained with the transformation of ATTC60483 strains with pZBlacZ plasmid, described above, were assayed during a batch growth in synthetic medium (Yeast Nitrogen Base with amino acids 13 g/l, glucose 50 g/l, G418 200 mg/l). Cells were pre-inoculated in the same medium of the experiment and inoculated in shake flasks (300 ml) containing 100 ml of fresh medium. Flasks were incubated in a shaking bath at 30° C., 200 rpm, and the fermentation was regularly monitored. Cell number was determined with an electronic counter (Coulter counter ZBI, Porro, D., Martegani, E., Tura, A., and Ranzi, B. M., (1991) Res. Microbiol., 142: 535–539), after the elimination of cellular aggregates with a sonication step (10 seconds, Fisher 300 sonicator, power 35%).

β-galactosidase activity was assayed as follows. About $10^8$ cells were collected, washed with water, and resuspended in 300 μl of Z-buffer: $Na_2HPO_4.2H_2O$ (0.06M), $NaH_2PO_4.H_2O$ (0.04M), KCl (0.01M), $MgSO_4.7\ H_2O$ (0.001M), β-mercaptoethanol (0.05M), pH 7. The cells were added to an equal volume of beads (SIGMA) (0.45–0.55 mm), and broken with three cycles: 1 min on vortex—1 min ice. Cellular debris were eliminated with a centrifugation at 12,000 rpm, 10 min. The supernatant was collected, and it constituted the total protein extraction. β-galactosidase activity was assayed with 10 μl of extract plus 390 μl Z-buffer, 100 μl ONPG (o-Nitrophenyl beta-D-galactopyranoside) 4 mg/ml, at 30 C. The reaction was stopped with 500 μl of 1 M $Na_2CO_3$, pH 11.

The protein concentration in the total extract was determined with Kit BIO-RAD Protein Assay (cat. 500-0001).

The enzymatic activity was calculated as:

$$U/ml = (\Delta E_{420}/min \times V.F.) \times (\epsilon \times d \times V.s.)^{-1}$$

where:

ε: molar extinction coefficient ($0.0045\ M^{-1}\ cm^{-1}$)

d: optical path (1 cm)

V.F.: final volume (ml)

V.s.: sample volume assayed (ml)

1 Unit is defined as the amount of enzyme that produces 1 mmol of o-nitrophenol/min at 30° C. Specific activity corresponds to 300,000 Units/mg.

No β-galactosidase activity was detected in the control strains, i.e. Zygosaccharomyces strains not transformed or transformed with pZygol.

EXAMPLE 5

Determination of the Stability of Plasmids pZygol and pZBlacZ in Cells Grown in Rich Medium, with or without Selective Pressure.

ATTC60483 cells transformed with pZygol or pZBlacZ were grown in rich media YEPD (Yeast Extract 10 g/l, Peptone 20 g/l, Glucose 20 g/l, G418 200 mg/l) to the stationary phase.

After the determination of the percentage of the population retaining the plasmid, 95±2% (see below), cells were transferred to fresh medium, without selective pressure (i.e. YEPD without G418), and were grown for 15 generations. Finally, the percentage of cells still retaining the plasmid was evaluated. In this way a low rate of plasmid loss per generation (16±2% per generation) was calculated for both plasmids.

Determination of the percentage of population retaining the plasmid. About 500 cells were transferred, after a sonication step (see above) onto YEPD plates, without any selection. Under these conditions, each viable cell gave rise to a clonal colony. After the colonies emerged, they were struck onto a YEPD plate containing G418. Therefore, only cells retaining the plasmid were able to grow. The percentage of cells having the plasmid in the original population was calculated as the ratio between the number of colonies in the two plates.

What is claimed is:

1. A strain of *Z. bailii* transformed with an expression vector comprising an ARS sequence from *S. cerevisiae*, a CEN (centromeric) sequence from *Z. bailii* or *S. cerevisiae*, a gene coding for a protein, a promoter controlling the expression of the gene, and a marker.

2. A strain according to claim 1, produced by transforming *Z. bailii* ATCC36947, *Z. bailii* ATCC60483, or *Z. bailii* ISA1307 with an expression vector comprising an ARS sequence from *S. cerevisiae*, a CEN (centromeric) sequence from *Z. bailii* or *S. cerevisiae*, a gene coding for a protein, a promoter controlling the expression of the gene, and a marker.

* * * * *